(12) United States Patent
Schulz et al.

(10) Patent No.: US 7,987,721 B2
(45) Date of Patent: Aug. 2, 2011

(54) METHOD AND DEVICE FOR DETERMINING DEFECTS IN A TURBINE BLADE

(75) Inventors: Michael Clossen-von Lanken Schulz, Geldern (DE); Michael Opheys, Nettetal (DE)

(73) Assignee: Siemens Aktiengesellschaft, Munich (DE)

( * ) Notice: Subject to any disclaimer, the term of this patent is extended or adjusted under 35 U.S.C. 154(b) by 535 days.

(21) Appl. No.: 11/628,231

(22) PCT Filed: May 12, 2005

(86) PCT No.: PCT/EP2005/052155
§ 371 (c)(1),
(2), (4) Date: Dec. 14, 2007

(87) PCT Pub. No.: WO2005/119242
PCT Pub. Date: Dec. 15, 2005

(65) Prior Publication Data
US 2008/0250860 A1   Oct. 16, 2008

(30) Foreign Application Priority Data
Jun. 1, 2004   (EP) .................................... 04012922

(51) Int. Cl.
G01N 29/04 (2006.01)
G01N 29/24 (2006.01)

(52) U.S. Cl. .......................................... 73/620; 73/660
(58) Field of Classification Search ............ 73/596–600, 73/618, 625–627, 602, 620–622, 660
See application file for complete search history.

(56) References Cited

U.S. PATENT DOCUMENTS

| | | | | |
|---|---|---|---|---|
| 4,335,600 A | * | 6/1982 | Wu et al. .................... | 73/112.03 |
| 5,365,787 A | * | 11/1994 | Hernandez et al. ............ | 73/660 |
| 5,423,220 A | * | 6/1995 | Finsterwald et al. .......... | 73/642 |
| 5,426,980 A | * | 6/1995 | Smith ............................ | 73/644 |
| 5,431,053 A | * | 7/1995 | Fink .............................. | 73/602 |
| 5,913,243 A | | 6/1999 | Hopeck et al. | |
| 6,019,001 A | | 2/2000 | Schreiner et al. | |
| 6,237,419 B1 | * | 5/2001 | Suh et al. ....................... | 73/642 |
| 6,523,418 B2 | * | 2/2003 | Bray .............................. | 73/801 |
| 6,813,950 B2 | * | 11/2004 | Glascock et al. .............. | 73/633 |
| 7,010,982 B2 | * | 3/2006 | Bergman ....................... | 73/618 |

FOREIGN PATENT DOCUMENTS

| | | |
|---|---|---|
| CN | 1055602 A2 | 10/1991 |
| DE | 84 18 008 | 11/1985 |
| DE | 35 30 595 A1 | 3/1987 |
| DE | 37 31 947 A1 | 4/1989 |
| DE | 44 21 277 A1 | 4/1995 |
| EP | 0 337 700 A2 | 10/1989 |
| EP | 0 635 719 A2 | 1/1995 |
| EP | 0381848 B1 | 8/1997 |
| JP | 61155855 A | 7/1986 |

(Continued)

OTHER PUBLICATIONS

J. Krautkramer and H. Krautkramer, "Werkstoffprufung mit Ultraschall" (Material Testing with Ultrasonics), Springer-Verlag, 1986, pp. 708.

*Primary Examiner* — Helen C. Kwok (57) ABSTRACT

The invention relates to a method and a measuring and evaluation device for determining defects in a turbine blade and to a fixing device for fixing a probe to a turbine blade surface.

12 Claims, 7 Drawing Sheets

FOREIGN PATENT DOCUMENTS

| | | |
|---|---|---|
| JP | 62261955 A | 11/1987 |
| JP | 01299456 A | 12/1989 |
| JP | 2004077357 A | 3/2004 |
| RU | 2072519 C1 | 1/1997 |
| RU | 2153602 C1 | 7/2000 |
| SU | 1439486 A1 | 11/1988 |
| WO | WO 85/02464 A1 | 6/1985 |
| WO | WO 2004/025290 A1 | 3/2004 |

* cited by examiner

METHOD AND DEVICE FOR DETERMINING DEFECTS IN A TURBINE BLADE

CROSS REFERENCE TO RELATED APPLICATIONS

This application is the US National Stage of International Application No. PCT/EP2005/052155, filed May 12, 2005 and claims the benefit thereof. The International Application claims the benefits of European Patent application No. 04012922.3 filed Jun. 1, 2004. All of the applications are incorporated by reference herein in their entirety.

FIELD OF INVENTION

The invention relates to a method and a measuring and evaluation device for determining defects in a turbine blade and to a fixing device for fixing a probe to a turbine blade surface.

BACKGROUND OF THE INVENTION

It is generally known that defects, e.g. in the form of cracks, have a negative effect on the strength of a component and thus also the reliability of the component. Under certain conditions, such cracks in the surface of components may grow. This applies, in particular, in the case of components such as, e.g. shafts, turbine blades or, in particular, turbine blade roots which, apart from static loading, also experience dynamic loading.

Methods for determining defects in components are represented in DE 44 21 277 A1, DE 37 31 947 A1, WO 85/02464 A1 and EP 0 337 700 A2. In the aforementioned documents, the dye penetration method used for crack testing a surface is described in each case. In these methods, a contrast medium is applied to the surface to be tested for cracks, which penetrates into existing cracks. The contrast medium is removed, the surface is cleaned, if necessary, and a developer is applied with a thin layer thickness. The contrast medium which has penetrated into the cracks becomes mixed with a developer at the geometric locations of the cracks so that the crack contour is rendered visible due to the thin layer of the developer. For this purpose, the developer, for example, has a white color and the contrast medium has a red color or the contrast medium is fluorescent.

Using the aforementioned method, however, it is not possible to investigate the roots of turbine blades in the installed state.

A further method for determining defects in components is represented in the book "Werkstoffprüfung mit Ultraschall" (Material testing with Ultrasonics), J. & H. Krautkrämer, Springer-Verlag Berlin 1986. In particular, it is described on pages 110 to 111 how a component area can be examined by means of ultrasound with a transmit probe and a receive probe by utilizing the reflection of an internal area in the component. When outsides of the component are opposite one another, the probes are arranged opposite one another on these outsides. The transmit probe sends the ultrasonic signal to the area to be examined. From there it is reflected to the receive probe. A further possibility of examination is the tandem method in which both probes are arranged behind one another on the same outside. In this arrangement, a component backside is utilized for a second reflection. However, none of the methods described can be used if there is only one accessible outside of the component and, in addition, there is no suitable backside for the additional reflection according to the tandem method.

A further method for determining defects in components is the so-called eddy current test method. In this method, an alternating magnetic field which produces eddy currents in the material to be tested is generated by means of an exciter coil. The eddy currents, in turn, result in an alternating magnetic field which is measured by means of a detector coil. Material faults in the form of defects have a characteristic influence on the magnetic field measured and can thus be detected.

Stress corrosion cracks or defects can lead to progressive damage in the case of dynamic loading of rotating parts such as, e.g. a wheel disc on a rotor of a turbine. It is necessary, therefore, to check such components for defects and stress corrosion cracks in predetermined intervals. For economic reasons, wheel discs and turbine blade roots or turbine blades which are arranged secured against twisting by axial or radial pins on a rotor cannot be tested by taking the rotor apart or dismantling the turbine blades. It is advisable, therefore, to perform ultrasonic testing in the area of the shrink fits and the adjoining material areas, particularly in the area of the inner hub surface and the axial torsion locks in the case of wheel discs. However, the geometry of the wheel disc is extremely complicated for an ultrasonic test with ultrasonic probes in the inaccessible inner hub area and in the vicinity of torsion locks. Moreover, the reproducible performance of ultrasonic tests also encounters other problems. The only available coupling surface for the ultrasonic probes are the side cheeks of the wheel disc. The accessibility to the coupling surfaces on the wheel disc is frequently restricted by adjacent wheel discs. A further problem consists in that the sound paths to geometry-related reflectors and to any cracks which may be present and emanate from the hub hole can be identical.

SUMMARY OF INVENTION

It is the object of the invention, therefore, to specify a method and a measuring and evaluation device and a fixing device in order to be able to determine defects of turbine blades in the installed state on a rotor.

The object directed towards the method is achieved by a method for determining defects in a turbine blade which is characterized by the following steps:
 fixing a probe over the turbine blade surface,
 connecting the probe to a measuring and evaluation device,
 measurement by means of a phased-array ultrasonic test method wherein an ultrasonic pulse signal is emitted and an echo signal caused by reflections on defects or shape boundaries is received,
 comparing the echo signal with a reference echo signal,
 determining defects by evaluating differences between the echo signal and the reference echo signal.

The object directed towards the measuring and evaluation device is achieved by a measuring and evaluation device for determining defects in turbine blades, comprising
 a fixing device for fixing a probe to the turbine blade surface,
 an ultrasonic pulse signal source connected to the probe,
 an ultrasonic echo signal receiver, and
 a display device for displaying the echo signal.

The object directed to the fixing device is achieved by a fixing device for fixing a probe to a turbine blade surface, wherein the fixing device is produced from an easily deformable material.

The advantage of the invention can be seen in that, among other things, defects in turbine blades can be determined in the installed state. There is no time consuming and thus costly dismantling and installation of the turbine blades.

The proposed use of probes which are constructed as phased arrays enables the direction of the radiated ultrasound or the direction from which the ultrasound can be received to be changed.

As a result of this method, it is possible, for example, to perform reliable and fast analyses in an expected fault area of turbine blade roots. Cracks are produced by high mechanical, thermal or corrosive loading. This results in fatigue or vibration cracks. The method presented enables faults which have occurred to be detected early and subsequently monitored.

The method presented provides reproducible test results and is suitable for practical use.

In an advantageous embodiment of the invention, a pulse echo method is used as a phased-array ultrasonic test method.

The pulse echo method makes it possible to determine very precise defects.

The invention is based on the fact that the probe is fixed over the turbine blade surface. In this arrangement, the probe is fixed in such a manner that after the probe has been detached and subsequently reattached, it assumes exactly the same position as before the removal of the probe. The probe must be positioned very accurately. This is the only way to provide reproducible measurements. During a measurement, an ultrasonic pulse signal is emitted by the probe and an echo signal originating from reflections on defects or shape boundaries is received.

By comparing the echo signal with a reference echo signal, defects can be determined by evaluating differences between the echo signal and the reference echo signal.

The reference echo signals are advantageously determined from model calculations or from measurements on an essentially defect-free turbine blade.

Using a probe constructed as phased array enables the ultrasonic pulse signal to be sent out in different directions. This provides a possibility for performing so-called angle scans of a relatively large angular range. It is thus possible to examine a larger area of the turbine blade during a measuring process.

The angular range is advantageously between −45° to +45° with respect to a main direction of irradiation, wherein the main direction of irradiation extends essentially perpendicularly to the turbine blade surface at the location of the probe.

The invention is based on the fact that a fixing device is used for fixing a probe to a turbine blade surface. This fixing device makes it possible to accommodate a probe and to position this probe very precisely on the turbine blade surface. Even after the fixing device has been removed and subsequently attached to the turbine blade surface, the probe assumes exactly the same position as before the removal of the fixing device.

In this arrangement, the fixing device is produced of an easily deformable material. This provides the advantage that the fixing device can be produced quickly and inexpensively.

The fixing device is advantageously produced of plastic, wood or rubber.

In an advantageous development of the invention, the fixing device is produced in such a manner that the outer geometric shape of the fixing device facing the turbine blade surface is adapted to the outer geometric shape of the turbine blade surface and the fixing device has a recess for accommodating the probe.

Adapting the fixing device to the outer shape of the turbine blade surface, which virtually leads to a negative impression mold, makes it possible to attach the probe always at the same place of the place of the turbine blade root to be tested.

The fixing device is suitably constructed to be easily attached.

To provide for better attachment and for good transmission of the ultrasound, an easily deformable ultrasonic transmission paste is applied between the fixing device and a turbine blade surface.

BRIEF DESCRIPTION OF THE DRAWINGS

Exemplary embodiments of the invention are represented by means of the figures. In the figures, functionally similar components are designated by the same reference symbols.

DETAILED DESCRIPTION OF INVENTION

Figure 1:
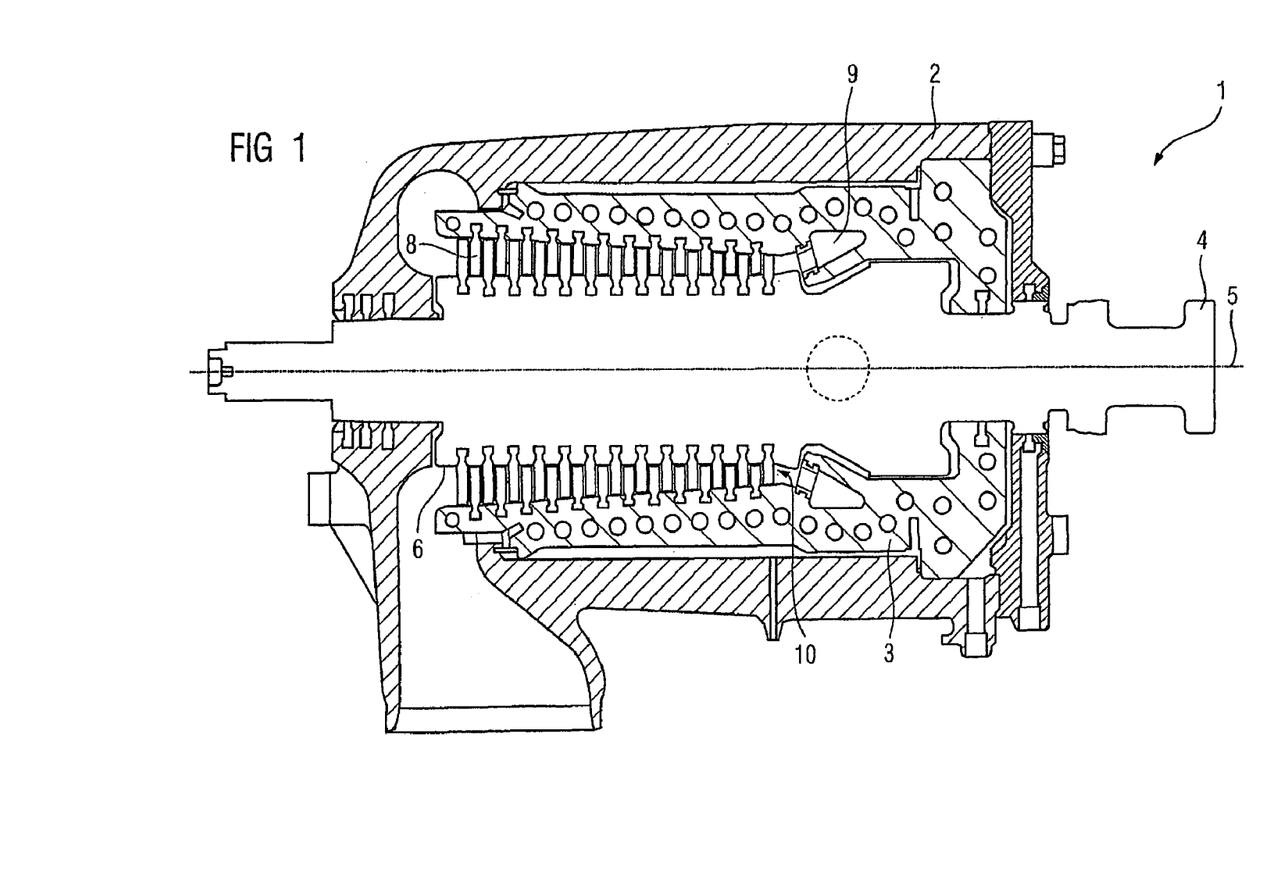
FIG. 1 shows a sectional view through a steam turbine.

FIG. 1 shows a section through a steam turbine 1. The steam turbine 1 has an outer casing 2 and an inner casing 3. A shaft 4 is supported rotatably about an axis of rotation 5. On the shaft surface 6, turbine blades 7 are arranged in the circumferential direction. In the inner casing 3, turbine guide blades 8 are arranged. In operation, steam flows into an admission area 9 and expands when passing through a flow duct 10. During this process, a rotation is imparted to the shaft 4. As a result, a rotor, not shown in greater detail, of a generator can be placed into rotation.

In inspection cases or in cases of damage, the outer casing 2 of the steam turbine 1 is opened, as a rule, to provide access to the individual turbine blades 7 on the shaft 4.

Figure 2:
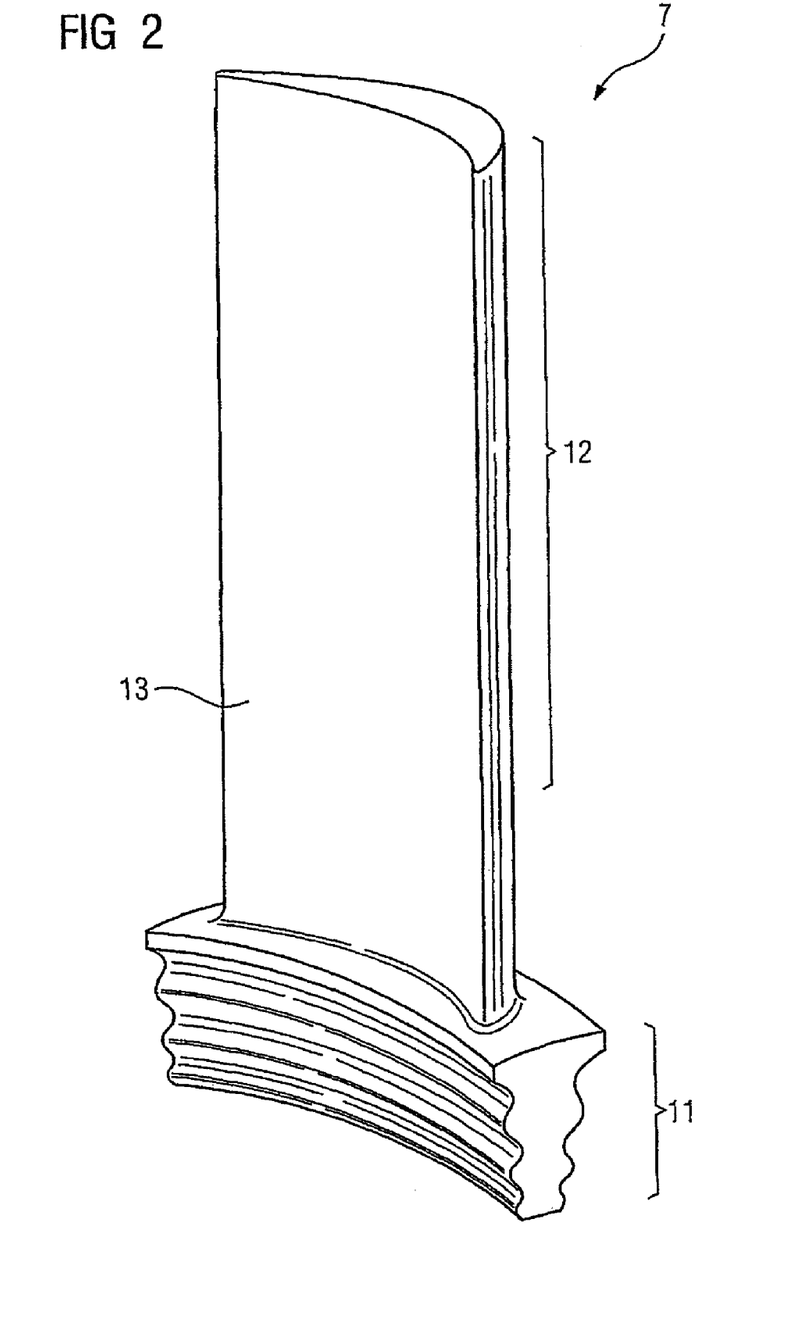
FIG. 2 shows a perspective view of a turbine blade.

FIG. 2 shows a perspective view of a turbine blade 7. The turbine blade 7 has a turbine blade root 11. The turbine blade root 11 shown in FIG. 2 is constructed as so-called Christmas tree root. When the steam turbine 1 is operated, high centrifugal forces occur due to the high rotational speeds of the shaft 4. The high centrifugal forces can lead to defects in the form of cracks in the turbine blade roots 11 or even in an upper turbine blade part 12.

In most cases, small defects in the form of cracks cannot be seen with a naked eye. The cracks can occur both on a turbine blade surface 13 and in the interior of the turbine blade 7.

Figure 3:
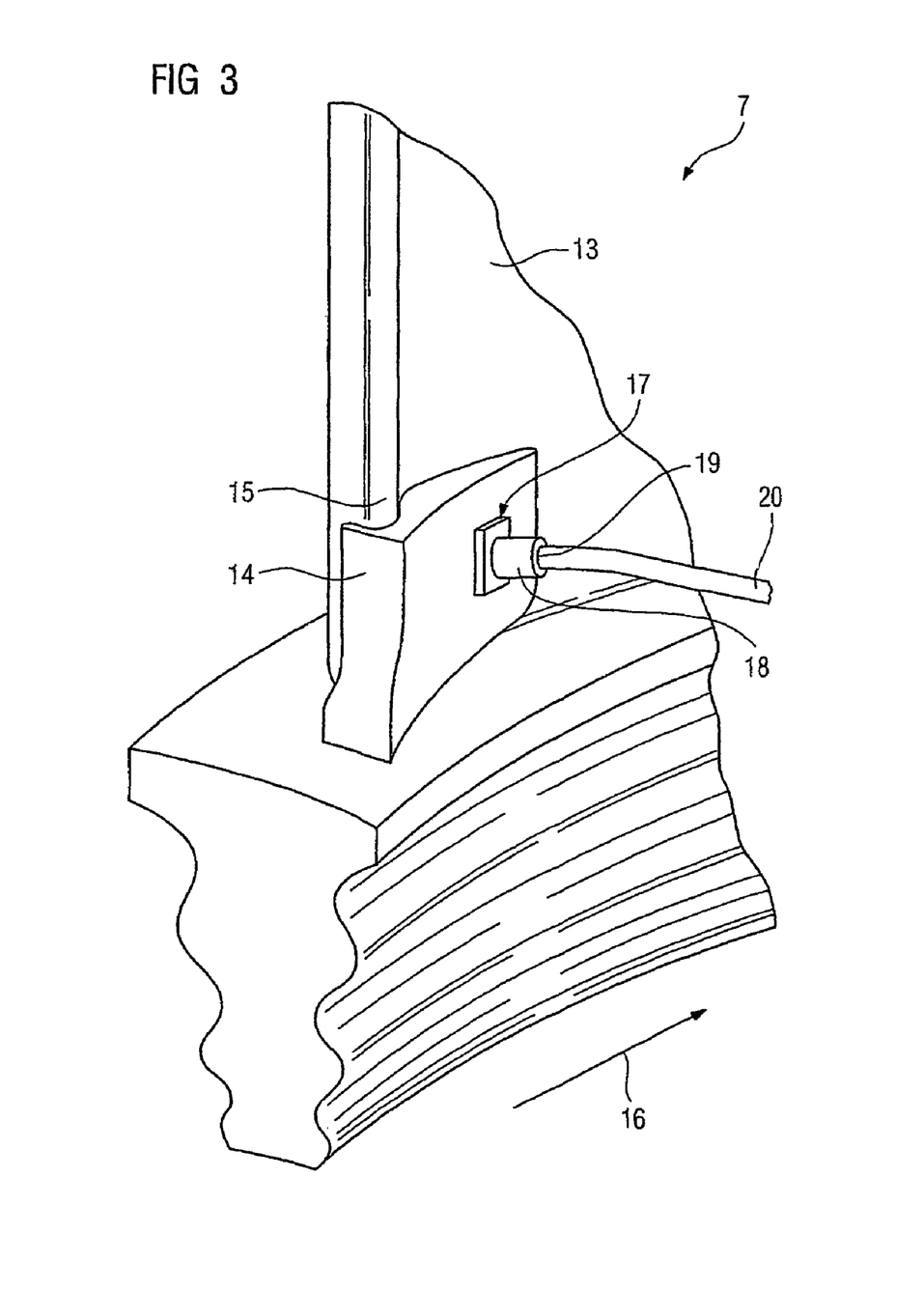
FIG. 3 shows a perspective view of a part of a turbine blade with a fixing device.

FIG. 3 shows a perspective view of a part of the turbine blade 7 and of a fixing device 14. The fixing device 14 is produced from an easily deformable material. The fixing device can be produced from plastic, wood or rubber. The fixing device can also be produced of a casting material which becomes rigid after curing.

The fixing device 14 is produced in such a manner that the outer geometric shape of the fixing device 14 facing the turbine blade surface 13 is adapted to the outer geometric shape of a section of the turbine blade surface 13. As can be seen from FIG. 3, the fixing device 14 is supported on a turbine blade edge 15. As a result, it is not possible to displace the fixing device in a direction of displacement 16. When the fixing device 14 is removed from the turbine blade 7, it can be attached again to precisely the same place.

The fixing device 14 has a recess 17 in which a probe 18 is arranged in such a manner that a passage for the ultrasonic rays is produced. The probe is installed in a recess 17 in such a manner that, on the one hand, the probe is clamped mechanically firmly in the fixing device or otherwise held and, on the other hand, rests as closely as possible on the turbine blade surface 13 so that the transmission of the ultrasonic waves is as free of interference as possible. The probe 18 has a probe output 19 which is connected to a measuring and evaluation device 21 via a line 20. The fixing device 14 is mounted on the turbine blade surface 13 by means of an easily deformable ultrasonic transmission paste.

The ultrasonic transmission paste used can be, e.g. an ultrasonic gel or adhesive.

As a result, the fixing device 14 can be constructed to be easily attachable.

Due to the outer shape of the fixing device 14, no complicated attachment is necessary. The ultrasonic transmission paste makes it possible to fill very small air gaps as a result of which an ultrasonic signal can easily penetrate into a material. The seating of the fixing device can be checked directly by means of the echo signals.

Figure 4:
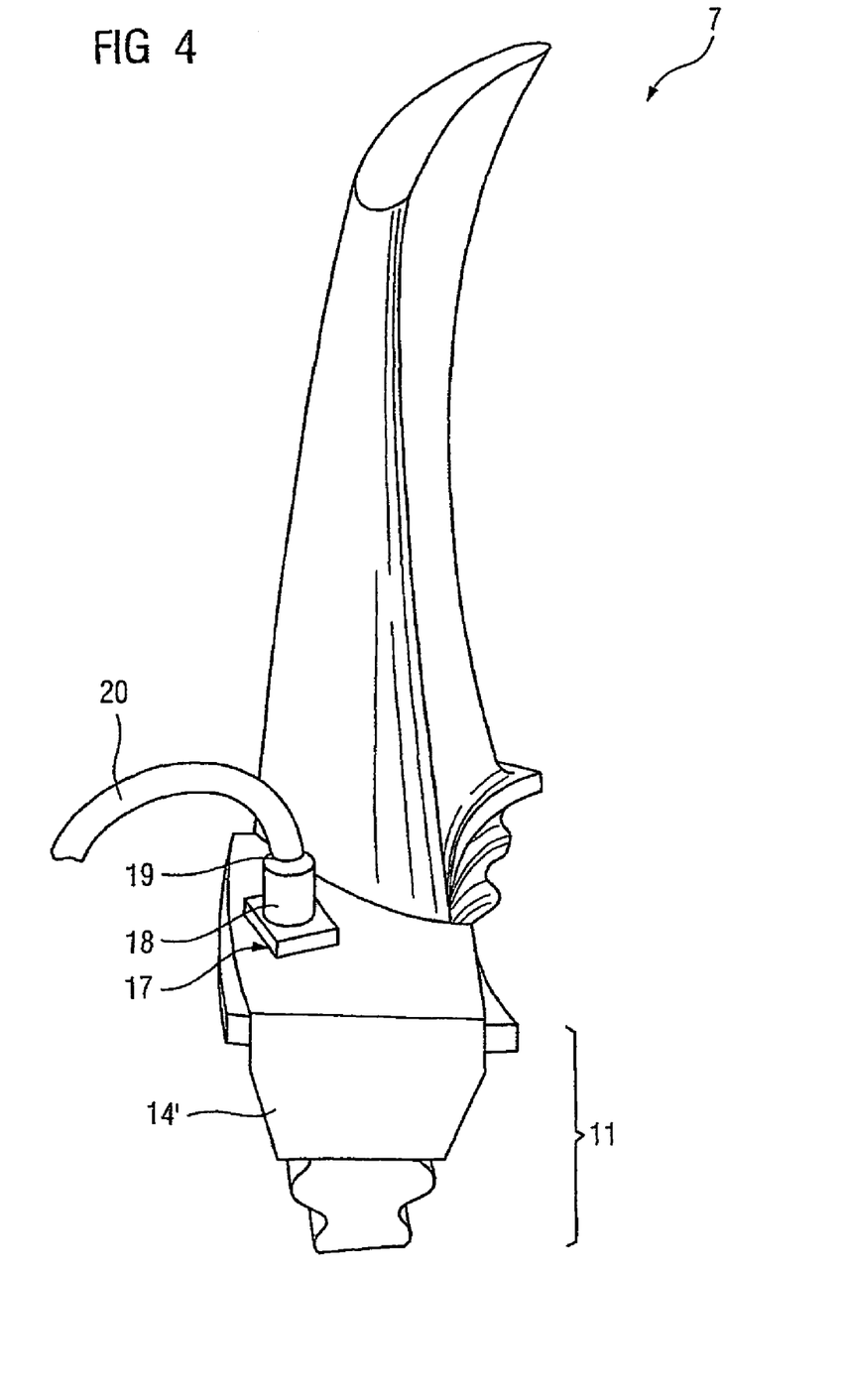
FIG. 4 shows a further perspective view of a part of a turbine blade with a fixing device.

FIG. 4 shows a further perspective view of a turbine blade 7 with a fixing device 14. The outer shape of the fixing device 14' shown in FIG. 4 is not identical with the outer shape of the fixing device 14 shown in FIG. 3. As represented in the description for FIG. 3, the habit of the fixing device 14 is adapted to a particular section of the turbine blade surface 13. The fixing device 14, 14' forms a negative mold of the section of the turbine blade surface 13, as it were.

Figure 5:
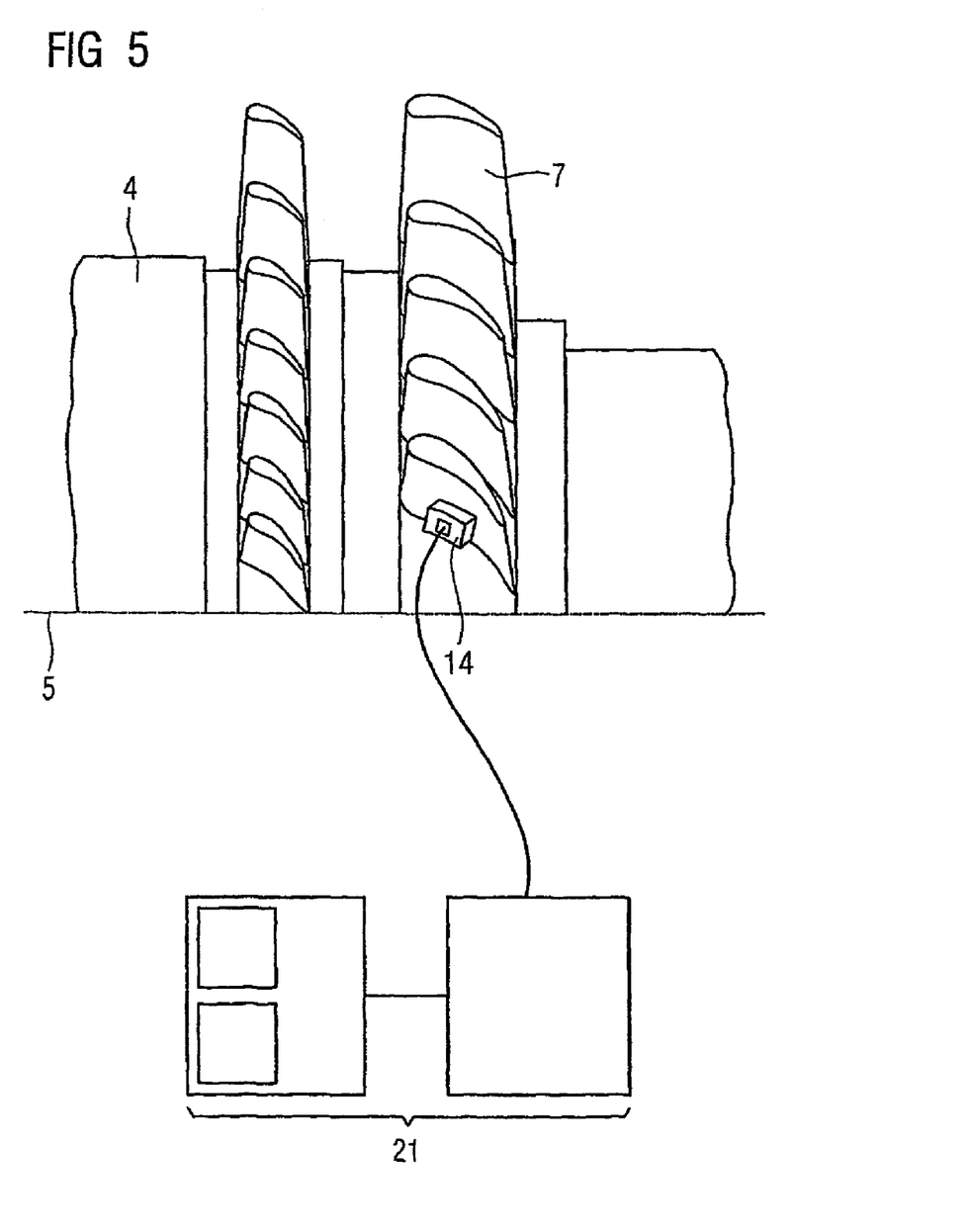
FIG. 5 shows a perspective view of a part of a rotor and of a measuring and evaluation device.

FIG. 5 shows a perspective view of a part of a shaft 4 with turbine blades 7. The fixing device 14 arranged at a place on the turbine blade 7 is connected to a measuring and evaluation device 21 via a line 20. The probe 18 is constructed as a phased array probe.

During a test of the turbine blade 7, the probe 18 emits an ultrasonic wave in one direction. The ultrasonic wave is reflected from defects or shape boundaries and detected as echo signal by the probe 18. The echo signal is forwarded to the measuring and evaluation device 21. Thus, a pulse-echo method is used. In alternative embodiments, the so-called pitch catch method can also be used in which a probe sends an ultrasonic signal and another probe receives this signal.

Using a probe constructed as phased array makes it possible to send out the ultrasonic pulse signal in different directions. This makes it possible to perform so-called angle scans over a relatively large angular range. In preferred embodiments, the angular range is between −45° to 45° with respect to a main direction of irradiation, the main direction of irradiation extending essentially perpendicularly to the turbine blade surface at the location of the probe. In particularly preferred embodiments, the angular range is between −85° to 85° with respect to the main direction of irradiation.

Figure 6:
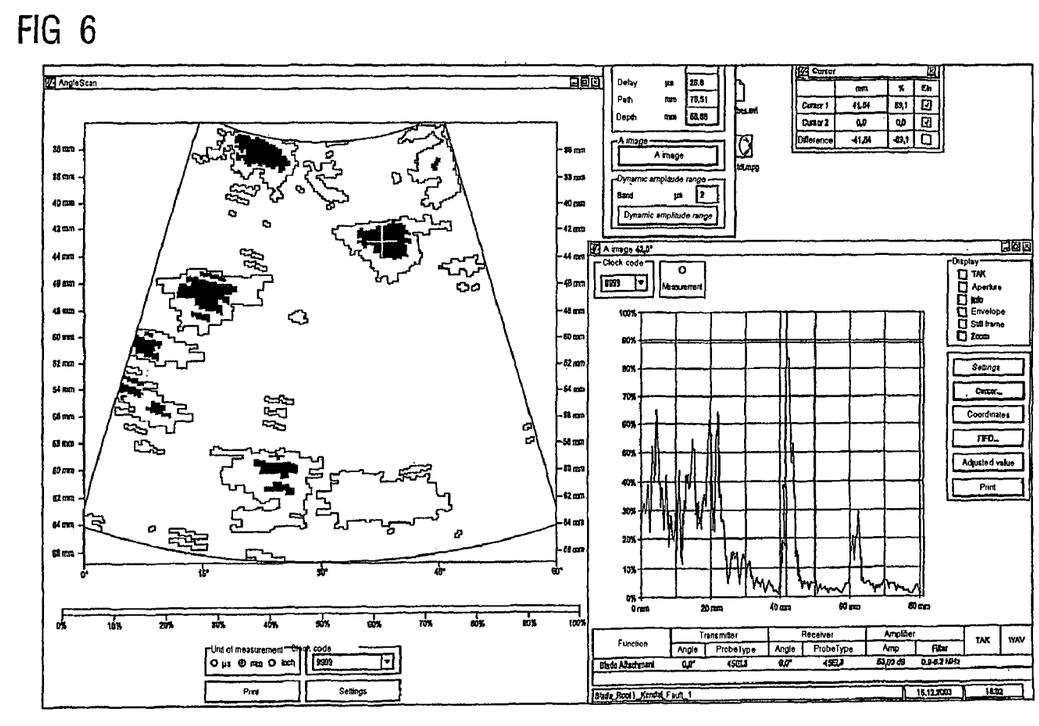
FIG. 6 shows a representation of a measurement recording with representation of a defect.

FIG. 6 shows the result of such a measurement. In the left-hand part of FIG. 6, a so-called angle scan is shown. In this scan, the ultrasonic wave has been sent out by the probe in an angular range between 0 and 80°. The dark spots in the angle scan show reflections on shape boundaries or defects. In the right-hand part of FIG. 6, a so-called A image can be seen. An A image shows the determined or measured intensity of the echo signal in dependence on the propagation time of the ultrasound or the distance, determined from this, from the probe to a shape boundary or a defect.

Figure 7:
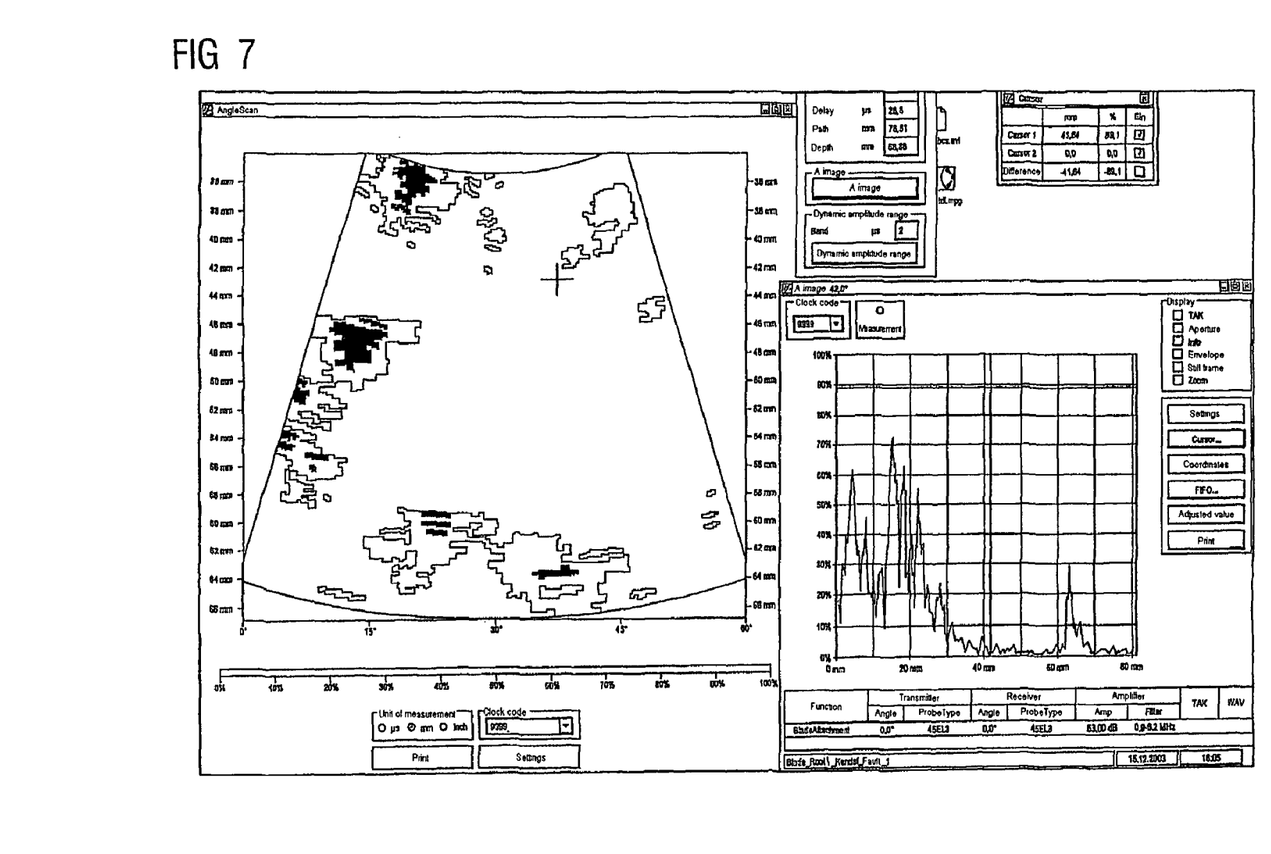
FIG. 7 shows a representation of a measurement recording of an essentially defect-free reference turbine blade.

FIG. 7 shows in the left-hand part an angle scan which has been recorded with the same probe 18 and the same fixing device 14. However, this recording was performed on a turbine blade 7 which does not have any defects. The dark spots in the angle scan are only caused by reflections on shape boundaries. The angle scan shown in the left-hand part of FIG. 7 can also be called a reference echo signal. A reference echo signal should be suitably determined not only on one defect-free turbine blade but on a number of these. In addition, it is appropriate to determine the reference echo signal from model calculations.

FIG. 7 shows that no echo signal was received at the place marked by the cross. By comparison, an echo signal has been unambiguously received at the place marked with a cross in FIG. 6. The remaining dark spots in the angle scan in FIG. 6 are almost identical with the dark spots in the angle scan of FIG. 7. The dark spot marked with the cross is unambiguously caused by a defect. This makes it possible to conclude the existence of defects in the turbine blade 7 by evaluating the differences between the echo signal and the reference echo signal. In alternative embodiments, the evaluation can be performed by image recognition software.

Model calculations are used as a preparatory measure for positioning the probe on the turbine blade surface 13. The model calculations are used for simulating what an echo signal to be expected looks like with a predetermined positioning of the probe 18.

The positions and angles of acoustic irradiation are determined by the aforementioned simulation.

For each area of the turbine blade 7 to be examined, an individual fixing device 14 is in each case produced. The fixing device 14 can also be called molded shoe. Depending on the type of blade, horizontally and/or vertically variable phase-array probes are used. Depending on application, areas of up to 35 mm around an expected fault area can be covered in only one angle scan and analyzed.

The theoretical examinations for determining the acoustic irradiation parameters, probe position and sound angles are performed with the aid of a 3D simulation. The parameters are established iteratively, i.e. probe positions of acoustic irradiation, angles of incidence and acoustic irradiation are varied until the theoretically most favorable conditions of impingement are achieved. For the visual display, corresponding simulations are performed on the computer. The method makes it possible to identify the fault position and the unambiguousness of the defect. The unambiguousness of the defect is achieved by a large signal-noise ratio. Apart from the angle of acoustic irradiation, transducer size and test frequency are important probe parameters. Angle of acoustic irradiation and transducer size are significantly determined by the blade root geometry or the size of the coupling surface, respectively. The test frequency must be selected in such a manner that a good fault resolution is achieved with a large signal/noise ratio. Transducer size and test frequency must be matched to one another in such a manner that faults in a disadvantageous position of acoustic irradiation can still be detected with the aid of a sound beam divergence. Variable parameters to be selected should be: location of acoustic irradiation, angle of acoustic irradiation. The probes 18 are integrated exchangeably in the fixing device 14.

A coupling surface on the turbine blade root 11 and the area of the turbine blade 7 necessary for testing must be free of coatings (corrosion, contamination etc.) and water repellent substances (grease, oil, etc.). The measurement data amplitude, sound propagation time and angle are stored by the measuring and evaluation device 21. The data can be called up repeatedly for post evaluation.

The invention claimed is:

1. A method for determining defects in a turbine blade, comprising:
configuring a probe fixing device for attachment to a portion of a blade surface and a portion of a blade root surface of a section of the turbine blade to be examined, wherein a surface of the probe fixing device is shaped to engage the portion of the blade surface and the portion of the blade root surface in a manner that fixes the probe fixing device into a particular position with respect to the section of the turbine blade to be examined;

attaching the probe fixing device over the section of the turbine blade to be examined;

attaching a probe to the probe fixing device;

connecting the probe to a measuring and evaluation device emitting an ultrasonic pulse signal by the probe;

receiving an echo signal reflected by defects or shape boundaries in the turbine blade via a phased-array ultrasonic test method;

comparing the received echo signal with a reference echo signal; and determining defects by evaluating differences between the echo signal and the reference echo signal.

2. The method as claimed in claim 1, wherein a pulse-echo method is used as the phased-array ultrasonic test method.

3. The method as claimed in claim 2, wherein the reference echo signal is determined from model calculations.

4. The method as claimed in claim 2, wherein the reference echo signal is determined from measurements on an essentially defect-free turbine blade.

5. The method as claimed in claim 4, wherein the probe is constructed as a phased-array probe where the ultrasonic pulse signal can be emitted in different directions.

6. The method as claimed in claim 5, wherein the ultrasonic pulse signal can be emitted in an angular range between −45° to +45° with respect to a main direction of irradiation that extends essentially perpendicularly to the turbine blade surface at the location of the probe.

7. A measuring and evaluation device for determining defects in turbine blades, comprising:

a probe;

a fixing device for attachment to a section of a turbine blade to be examined, wherein a rigid surface of the fixing device is preformed as negative impression of a portion of a blade surface and a portion of a blade root surface of the section of the turbine blade to be examined, wherein an interaction of the surface of the probe fixing device with the portion of the blade surface and the portion of the blade root surface fixes the probe fixing device into a particular position with respect to the section of the turbine blade to be examined;

an ultrasonic pulse signal source connected to the probe that provides an ultrasonic pulse signal;

an ultrasonic echo signal receiver that receives an ultrasonic echo signal; and a display device for displaying the echo signal.

8. The device as claimed in claim 7, wherein the probe is constructed as a phased-array probe.

9. The device as claimed in claim 8, wherein the fixing device is selected from the group consisting of plastic, wood and rubber.

10. The device as claimed in claim 9, wherein the fixing device has a recess for accommodating the probe.

11. The device as claimed in claim 10, wherein the fixing device is attachable to the blade surface and the blade root surface of the section of the turbine blade to be examined.

12. The device as claimed in claim 11, wherein the fixing device is attached to the blade surface and the blade root surface of the section of the turbine blade to be examined by a deformable ultrasonic transmission paste.

* * * * *